(12) United States Patent
Miller et al.

(10) Patent No.: US 7,963,945 B2
(45) Date of Patent: Jun. 21, 2011

(54) REPLACEABLE SUPPLIES FOR IV FLUID DELIVERY SYSTEMS

(75) Inventors: Casey T. Miller, Corvallis, OR (US); David R. Otis, Jr., Corvallis, OR (US); Christopher Vitello, Corvallis, OR (US); Mark McCarty, Corvallis, OR (US); Hardey Bhathal, Corvallis, OR (US); Joseph W. Dody, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1074 days.

(21) Appl. No.: 11/300,025

(22) Filed: Dec. 14, 2005

(65) Prior Publication Data
US 2007/0135765 A1 Jun. 14, 2007

(51) Int. Cl.
*A61M 37/00* (2006.01)
*A61M 31/00* (2006.01)

(52) U.S. Cl. ........................................ 604/131; 604/519
(58) Field of Classification Search .................. 604/131, 604/519; 417/394
See application file for complete search history.

(56) References Cited

U.S. PATENT DOCUMENTS

| | | | | |
|---|---|---|---|---|
| 4,966,579 A * | 10/1990 | Polaschegg | | 604/65 |
| 5,609,572 A * | 3/1997 | Lang | | 604/22 |
| 6,146,109 A | 11/2000 | Davis et al. | | |
| 6,733,252 B2 * | 5/2004 | Feygin et al. | | 417/394 |
| 6,875,208 B2 | 4/2005 | Santini et al. | | |
| 6,935,010 B2 | 8/2005 | Tadigadapa et al. | | |
| 7,029,455 B2 * | 4/2006 | Flaherty | | 604/131 |
| 7,442,181 B2 * | 10/2008 | Schubert et al. | | 604/65 |
| 2002/0045911 A1 | 4/2002 | Fletcher et al. | | |
| 2004/0223985 A1 | 11/2004 | Dunfield et al. | | |
| 2004/0254527 A1 | 12/2004 | Vitello et al. | | |
| 2005/0126304 A1 | 6/2005 | Sparks et al. | | |
| 2005/0149000 A1 | 7/2005 | Santini et al. | | |

FOREIGN PATENT DOCUMENTS

EP 0 824 022 A1 2/1998

OTHER PUBLICATIONS

Sarah Yang, Researchers developing MicroJet for ouchless injections, UC Berkeley Press Release, Mar. 16, 2005.
Aaron Alexander, Microelectromechanical Drug Delivery Systems, Northwestern University, Dec. 3, 2004.
Lauren Fletcher, Feasibility of an Implanted, Closed-Loop Blood-Glucose Control Device, Stanford University, Spring 2001.
Alireza Khademhosseini, Controlled-release Microchip Drug Delivery Systems: Past, Present and Future, University of Toronto, 2000.
ISSYS Inc., ISSYS Inc. Awarded $1.97 Million for the development of MEMS-based, ultra-accurate, portable, multi-drug infusion systems, Oct. 17, 2003.
Tom Henderson, Infusion Device Could Improve Drug Delivery, The Detroit News, Feb. 15, 2004.

* cited by examiner

*Primary Examiner* — Theodore J Stigell
*Assistant Examiner* — Imani Hayman

(57) ABSTRACT

The present invention is directed to an integrated cartridge assembly for delivery of the biocompatible fluids to a subject, in which the device comprises an integrated cartridge including a fluid reservoir for housing the biocompatible fluid, a dispenser permanently and fluidically connected to the fluid reservoir, and configured for dispensing the biocompatible fluid to a manifold which is fluidically and removably connectable to the cartridge.

18 Claims, 9 Drawing Sheets

REPLACEABLE SUPPLIES FOR IV FLUID DELIVERY SYSTEMS

FIELD OF THE INVENTION

The present invention generally relates to IV fluid delivery systems, in particular replaceable and disposable integrated drug supplies and systems including the same.

BACKGROUND OF THE INVENTION

In hospitals and other medical facilities, it is often necessary to administer medication to a patient by infusing the medication into the patient through a catheter that is connected to the circulatory system of the patient. Common infusion techniques include introduction of a solution including the medication directly to the patient, or introducing the medication solution in combination with an infusion fluid serving as a diluent. The infusion may involve dispensing the fluid to the subject by gravity or actively pumping the fluid into the subject using a device known as an infusion pumps.

Unfortunately, current systems for administering medication by way of infusion suffer from several disadvantages. By way of example, current systems require an assembly of many different pieces or components (e.g., IV Bags, tubing, drip chambers, y-site connectors, etc.) to achieve single or multi-drug delivery to the patient. Due to the cumbersome assembly of these components by the attending care taker (nurses, medics, physicians), most often at the bedside, significant attendant time is consumed to prepare the infusion equipment for use. Typically due to the large number of steps, interventions, and operations, the current solutions are prone to errors. These errors can lead to patient injury or death, increased litigation, increased insurance cost, and loss of patient trust.

There exists a need to reduce errors, set-up and operational time, and complexity of administration of IV infusion. The present invention addresses these needs and others.

SUMMARY OF THE INVENTION

The present invention is directed to devices and methods for delivery of biocompatible fluids to a subject. In an embodiment, the device is an integrated cartridge assembly for delivery of the biocompatible fluids to the a subject, in which the device comprises an integrated cartridge including a fluid reservoir for housing the biocompatible fluid, a dispenser permanently and fluidically connected to the fluid reservoir, and configured for dispensing the biocompatible fluid to a manifold which is fluidically and removably connectable to the cartridge. In an embodiment, the integrated cartridge includes a memory device.

BRIEF DESCRIPTION OF THE DRAWINGS

FIGS. 3 through 5A and 5B are schematic illustrations of exemplary IV infusion systems embodying features of the present invention.

DETAILED DESCRIPTION OF EMBODIMENTS OF THE INVENTION

Figure 1:
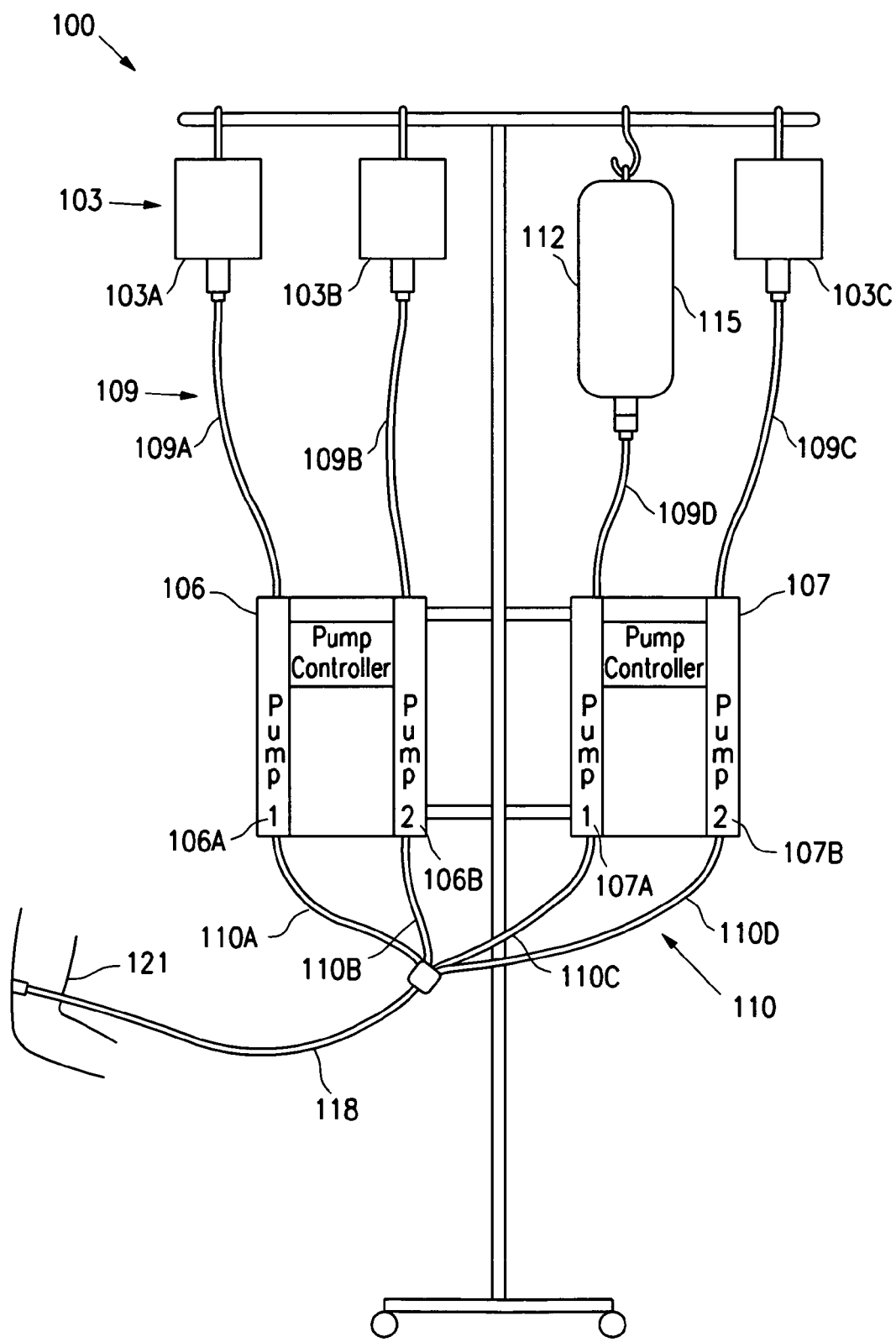
FIG. 1 is a schematic illustration of a current IV infusion system.

The present invention is directed to delivery of fluids, in particular biocompatible fluids such as infusion fluids and bioactive fluids (e.g., containing drugs) to patients, in care facilities such as homes, hospitals, or in a mobile environment such as an ambulatory vehicle.

In an embodiment, a device embodying features of the present invention is an integrated cartridge assembly for delivery of biocompatible fluids to a subject, comprising an integrated cartridge. The integrated cartridge includes a fluid reservoir for housing a biocompatible fluid; and a dispenser permanently and fluidically connected to the fluid reservoir, and configured for dispensing the biocompatible fluid to a manifold which is fluidically and removably connectable to the cartridge.

In an embodiment, the integrated cartridge provides for storage of data regarding information such as the drug, dosage, and potential drug incompatibilities in a memory device (e.g., memory chip, EEPROM (electrically erasable programmable read-only memory), flash memory device). In an embodiment, the memory device is integrated, preferably substantially permanently, with the integrated cartridge. The information may be stored (or written) onto the memory device at any suitable location, such as the place of manufacture, pharmacy, nursing station, ambulance, or the patient's beside.

In an embodiment, the memory device may be pre-programmed with the relevant information and travels with the integrated cartridge (including the drug supply). The information may be written to the memory device using a number of ways, as for example through physical connection with a PC (personal computer), IR (infrared) or RF (radio frequency) connection; hereafter referred to as the "encoder." In an embodiment, the drug supply is integrated with a dispensing mechanism.

In an embodiment the memory device is re-writable enabling modification of the information (e.g., modification of the dose) by the attending physician or nurse, or other authorized personnel. In an embodiment, an encoder may be present in the system controller box, as will be further described below.

Possible advantages obtained as a result of the use of devices embodying features of the present invention and methods using the same, independently include, but are not limited to, reduction in time associated with assembly of IV components at the bedside, reduction in time associated with programming of infusion system and pumps at bedside, reduction in errors associated with IV administration, reduction in pharmacy workload (e.g., when the drug supply is pre-configured with the necessary information without the need to specifically formulate the drug at the pharmacy), simplification of drug fulfillment logistics in the hospital or care facility, use of standard fill supplies, and more space-efficient fluid delivery systems improving the bedside environment for the patient and the care facility staff.

After one or more integrated cartridges are connected with an infusion system, the system controller box reads and/or interprets the stored information on the memory device.

In an embodiment, apparatus embodying features of the present invention and methods using the same, enable automated data management and communication and minimize or reduce the need for manual verification (and/or manual bar code scanning as the case may be), without requiring wired or wireless connectivity or extensive IT infrastructure to enable data automation.

As used herein, a group of individual members stated in the alternative includes embodiments relating to a single member of the group or combinations of multiple members. For example, the term "antibiotic, bronchodilator, or vitamin," includes embodiments relating to "antibiotic," "bronchodilator," "vitamin," "antibiotic and bronchodilator," "bronchodilator and vitamin," "antibiotic and vitamin," and "antibiotic, bronchodilator, and vitamin."

As used herein, a "bioactive fluid" comprises a bioactive composition including at least one bioactive substance or agent that affects a biological function of a subject to which it is administered. An example of a bioactive substance is a pharmaceutical substance, such as a drug or antibiotic, which is given to a subject to alter a physiological condition of the subject such as a disease. Bioactive substances, compositions, and agents also include, but are not limited to, other bio-molecules, such as proteins and nucleic acids, or liposomes and other carrier vehicles that contain the bioactive substances. As used herein the term "drug" includes any bioactive composition administered for a therapeutic (including diagnostic) purposes.

An used herein an "infusion fluid" includes any fluid, such as water or a saline solution, which is infused to a subject or patient. Examples of infusion fluids include Lactated Ringers solution, a saline solution of water and NaCl, and solutions such as D5W, a common IV fluid comprising water and 5% Dextrose by weight. An infusion fluid may be administered to a subject alone or as diluent for a bioactive fluid.

As used herein, the term "infusion" refers to the introduction of a fluid into a subject, such as the intravascular, intramuscular, intraorbital, subcutaneous, intrahepatic, intralymphatic, or intrathecal introduction of a fluid. The term infusion may include flowing or dripping the fluid into the subject by, but not limited to, gravity or pumping the fluid into the subject with the aid of a pump.

FIG. 1 illustrates an example of an existing IV infusion system 100 for delivery of three drug solutions 103 (103A, 103B, 103C); including two, dual-channel infusion pumps 106 and 107, each pump having two individual pumps 106A 106B, and 107A and 107B, respectively. The infusion pumps 106A and 106B of the dual-channel infusion pump 106, are connected to the two supplies of drug solutions, 103A and 103B; each connection being made through a dedicated IV (intravenous) conduit 109, such as tubings 109A and 109B.

The other infusion pumps 107A and 107B of the dual-channel pump 107, are connected to one container of drug solution 103C and one container of infusion fluid 112, such as a saline bag 115, each connection being made through dedicated IV (intravenous) conduits such as tubings 109C and 109D. The multiple tubings 110 are then merged into a single conduit such as tubing 118 for connection to a subject 121 (not shown) undergoing treatment.

Figure 2:
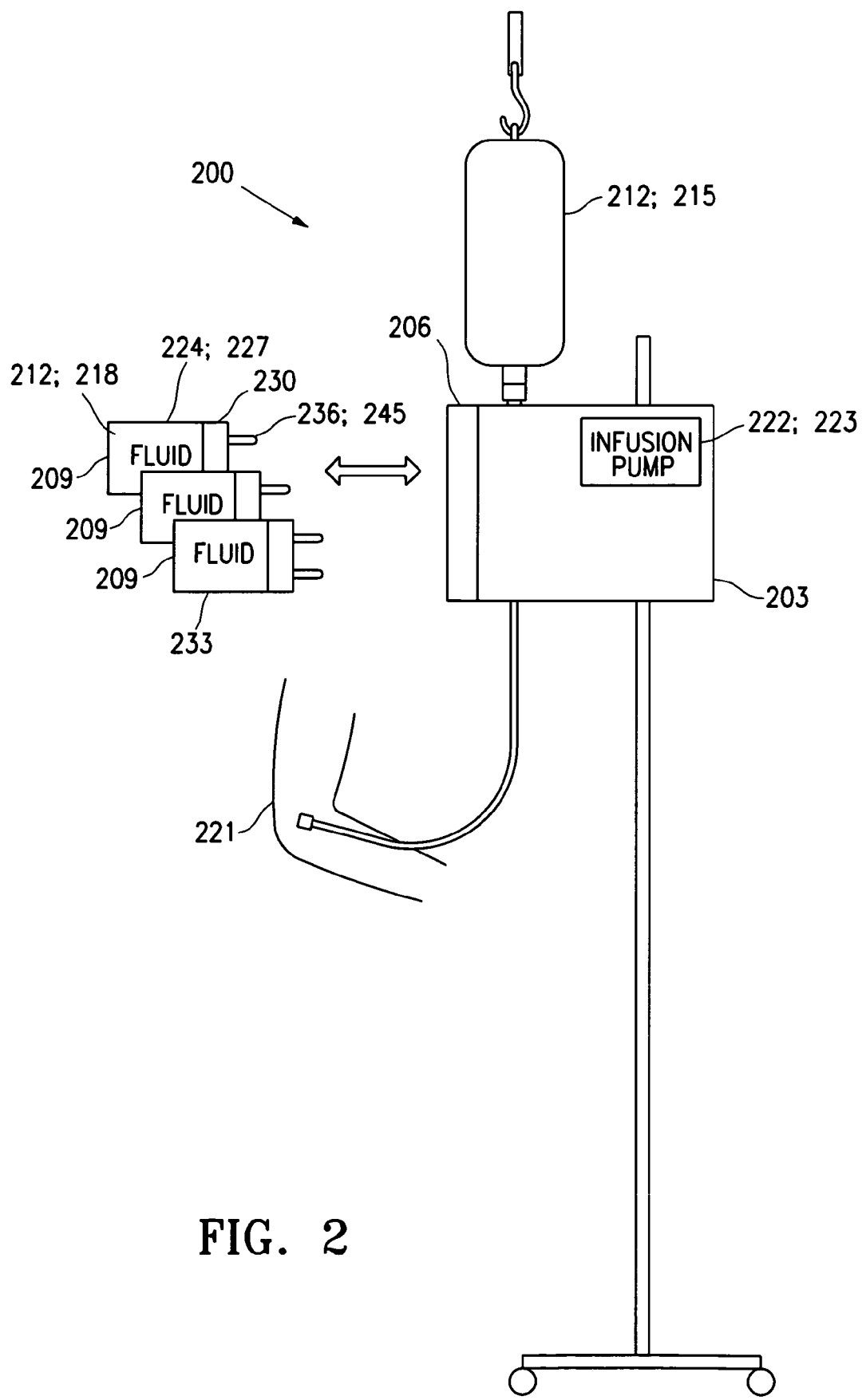
FIG. 2 is a schematic illustration of an exemplary IV infusion system embodying features of the present invention.

Now referring to FIG. 2, an infusion system 200 is schematically shown embodying features of the invention, and including a main system controller box 203, a manifold 206, and at least one integrated cartridge 209. In the embodiment shown, the infusion system 200, includes a plurality of integrated cartridges 209. The manifold 206 is fluidically connectable to at least one source of biocompatible fluid 212 such as infusion fluid 215 (e.g. saline solution). In an embodiment, the system controller 203 is a physical chassis which includes mechanical fixturing and electrical interconnects to receive one or more integrated fluid cartridges 209 for delivery of biocompatible fluids 212, such as bioactive fluid 218 (or infusion fluid 215 as described further below), to a subject 221.

The manifold 206, as will be further described below, is connectable to a pump 222, such as a peristaltic pump 223, which is external to the manifold (internal to the system controller box) for generating positive pressure to deliver at least one of the biocompatible fluids to the subject.

In the embodiment as shown, the integrated assembly 209 includes a fluid reservoir 224, stored within a fluid container 227, for housing the biocompatible fluid 212; and a dispenser 230 integrally and fluidically connectable to the fluid reservoir 224. In an embodiment, as shown, the dispenser 230 is substantially permanently, preferably permanently, and fluidically connected to the fluid reservoir 224. The fluid reservoir 224 and the dispenser 230, together, form an integrated fluid dispensing system 233. In the embodiment shown in FIG. 2, the integrated cartridge 209 further includes one or more cartridge fluid interconnects 236 for removably and fluidically connecting the integrated fluid dispensing system 233 to manifold fluid interconnects 239 (shown in FIGS. 3 and 4) of the manifold 206. The cartridge fluid interconnect 236 and manifold fluid interconnect 239, form a matched pair of fluid interconnect 242 (FIG. 5B), for receiving and dispatching fluids. By way of example, the cartridge fluid interconnect 236 and the manifold fluid interconnect 239 may comprise, a male component and a matching female component, respectively. The paired fluid interconnect 242 may be active, such as a needle 245 and an elastomeric septum 248 (FIG. 5B), allowing removal of integrated cartridge 209, during use, from the manifold 206 without introducing air or substantially hindering the introduction of air into and without displacing or substantially hindering the displacement of fluid out of the manifold 206.

In an embodiment the manifold 206 is located within or is attached to the system controller 203. In an embodiment either or both the integrated cartridge 209 and the manifold 206 are disposable. The disposability of the cartridge and/or manifold, enables, among other things, faster exchange of medication supply, ensuring sterility, and enabling delivery of a new bioactive fluid, which may be potentially incompatible with the bioactive fluid previously used. In an embodiment the integrated assembly 209 is configured to be refillable with the same biocompatible fluid 212, or a different biocompatible fluid (as for example when the cartridge may be re-used upon proper cleaning and sterilization, as necessary).

As used herein, the term "dispenser" may be used interchangeably with the term "pump" designating a device that can create fluid flow. Pumps are typically categorized into two groups, namely, positive displacement and dynamic pumps.

The positive displacement pump delivers a finite volume of fluid for each cycle of pump (DoE Fundamentals Handbook, Mechanical Science, Module 3, "Pumps", p. 28). Positive displacement pumps are typically classified into two categories: (1) reciprocating and (2) rotary. Piston, plunger and diaphragm pumps are examples of reciprocating pumps. Gear, vane, screw and lobe pumps are examples of rotary pumps. All of these pumps impart energy to the material pumped by trapping a fixed volume within an inlet and outlet and compressing the material. (Marks Standard Handbook for Mechanical Engineers, 10th Edition, Eugene Avallone, 1996, pg. 14-2.) Examples of positive displacement pumps can be found in the following U.S. Pat. No. 5,854,646 (diaphragm), U.S. Pat. No. 5,336,062 (microminiaturized pump) (electrostatic type), and U.S. Pat. No. 4,344,743 (piezoelectric driven diaphragm micro-pump).

Dynamic pumps impart velocity energy to the fluid which is converted to pressure energy upon exiting the pump. The most common dynamic pump is the centrifugal pump. Centrifugal pumps have rotating impellers within a case that receives liquid at an inlet and imparts velocity energy into pressure energy within the vanes causing fluid discharge (Marks Standard Handbook for Mechanical Engineers, 10th Edition, Eugene Avallone, 1996, pg. 14-16). Other examples of dynamic pumps include acoustic, thermal ejection (inkjet), and magnetic pumps. Examples of dynamic pumps can be found in the following U.S. Pat. No. 6,210,128 (Fluidic drive for miniature acoustic fluidic pumps and mixers), and U.S. Pat. No. 6,408,884 (Magnetically actuated fluid handling devices for microfluidic applications).

Figure 3:
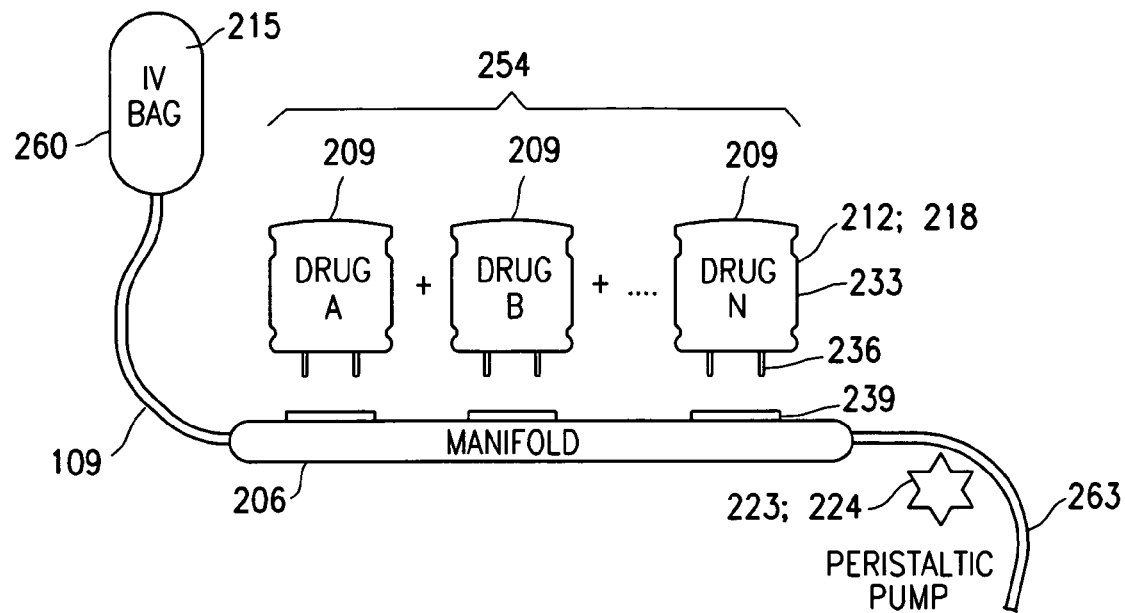
Figure 4:
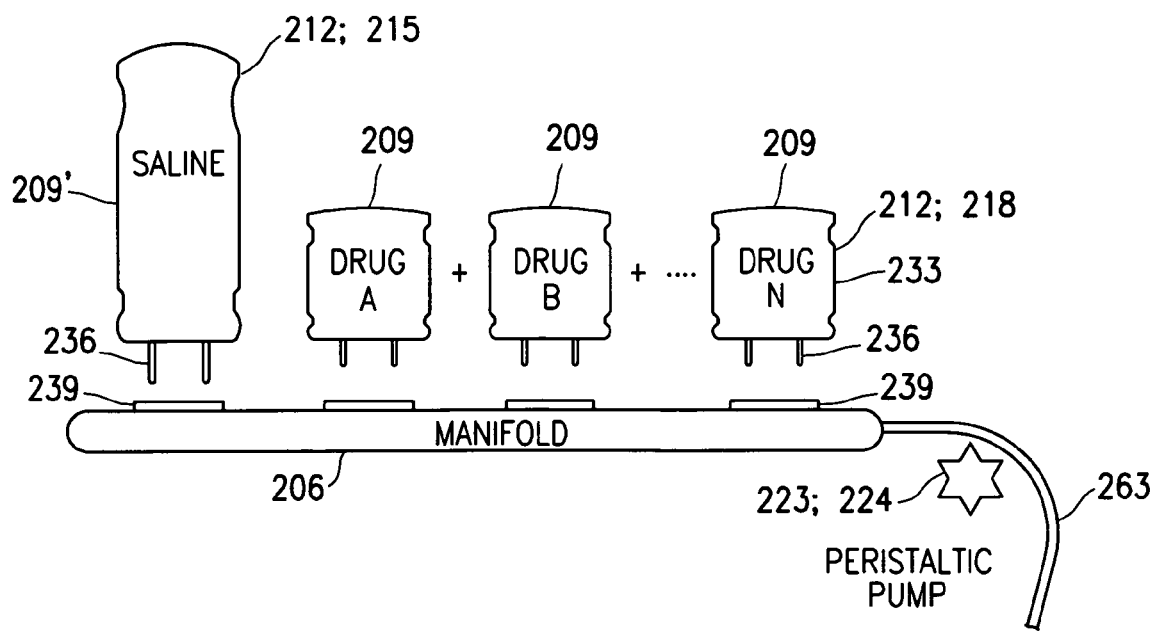
Figure 9:
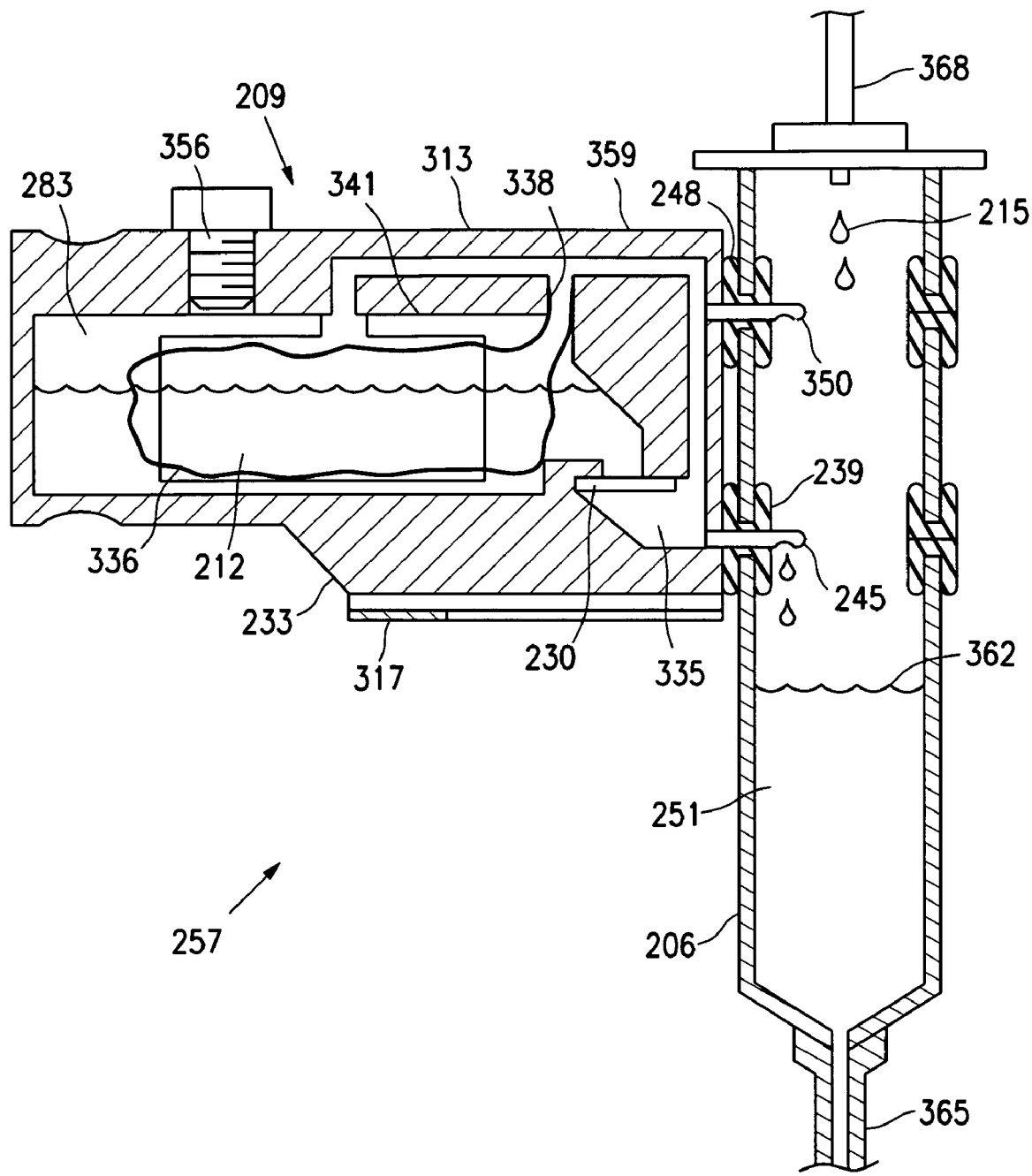
FIG. 9 is a schematic illustration of an alternate integrated cartridge embodying features of the present invention.

The manifold 206, as is shown in more detail in FIGS. 3 through 5 (and 5A and 5B), includes a receptacle 251 for receiving and dispatching biocompatible fluids 212 and includes at least one manifold fluid interconnect 239 (as for example shown in FIGS. 9 and/or 5B) for fluidically coupling the receptacle 251 to an assembly 254 of integrated cartridges 209. As shown, the integrated cartridge assembly 254 includes a plurality of integrated cartridges 209, each with at least one integrated fluid dispensing systems 233. The manifold 206 is configured for maintaining sterility and system pressure. In an embodiment, the one or more integrated fluid dispensing systems 233 and the manifold 206 form, together, a fluid delivery system 257 (FIG. 9).

Figure 5A:
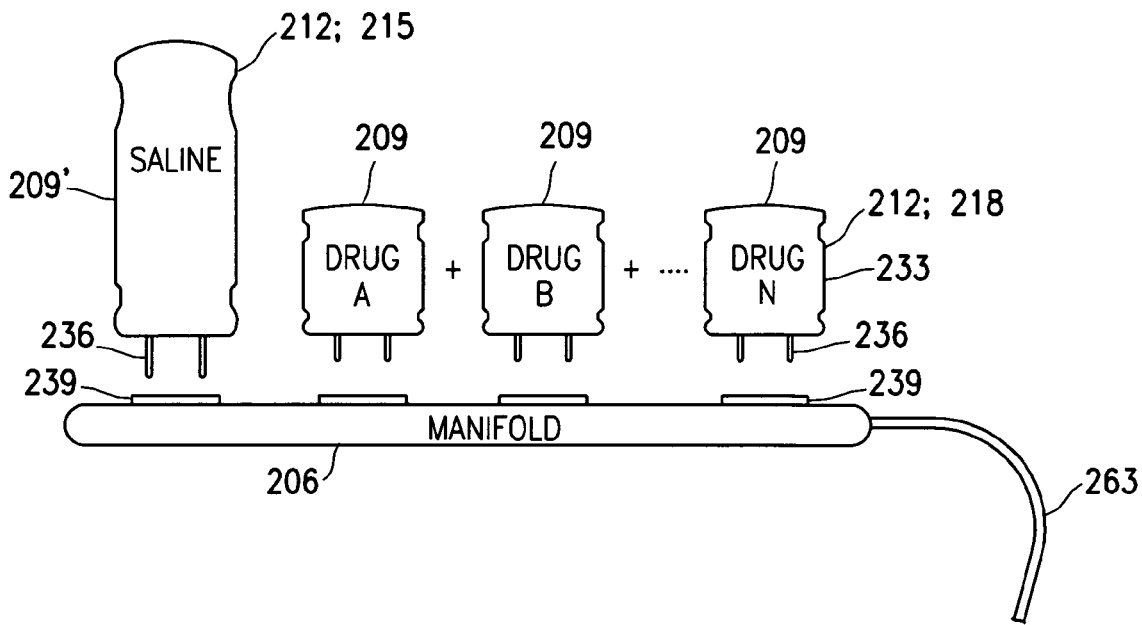
Figure 5B:
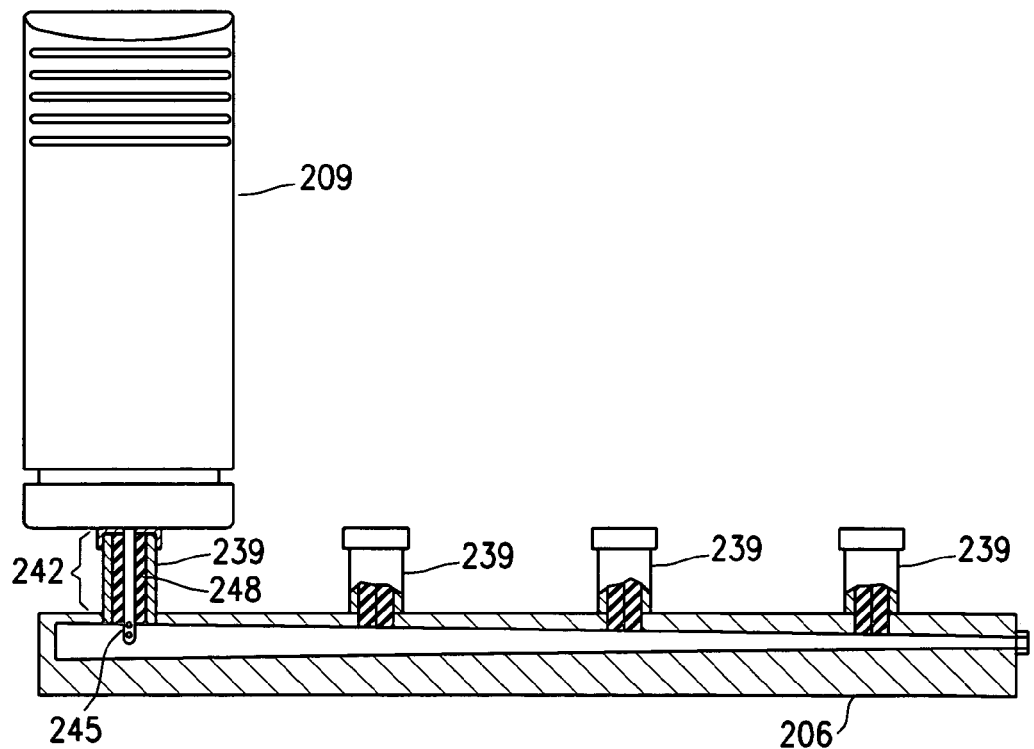

In one exemplary embodiment, features of which are shown in FIG. 3, cartridge fluid interconnects 236 fluidically connect each of the integrated cartridges 209 to the manifold 206 via corresponding manifold fluid interconnects 239 (as for example shown in FIG. 5B). An infusion fluid supply bag 260 is fluidically connected to the manifold receptacle 251 through IV tubing 109 providing a source of infusion fluid such as water or saline 215. The Manifold 206 is fluidically connected to a pump 223 external to the manifold, such as peristaltic pump 224 via manifold outlet conduit 263, for final and/or additional control of the rate of delivery and delivery pressure of the combined fluids.

In one embodiment, features of which are shown in FIG. 4, several integrated cartridges, 209, are configured to house biocompatible fluids such as a bioactive fluid 218 and are connected to the manifold 206. In the embodiment shown, one integrated cartridge 209 includes a biocompatible fluid 212 such as infusion fluid 215. Cartridge fluid interconnects 236, connect the integrated cartridges 209 to the manifold 206 via coupling with the manifold fluid interconnects 239. The Manifold 206 outlet conduit 263 is fluidically connected to the pump 223, such as the peristaltic pump 224, allowing for final and/or additional control of the rate of delivery and delivery pressure of the combined fluids.

In one embodiment, features of which are shown in FIGS. 5A and 5B, several integrated cartridges 209; include biocompatible fluids 212 such as bioactive fluid 218 and an infusion liquid 215 (in integrated cartridge 209'); are connected to the manifold 206. Cartridge fluid interconnects 236 connect the integrated cartridges 209 (and/or 209') to the manifold 206 via coupling with the manifold fluid interconnects 239. The integrated cartridges 209, in this embodiment, include a positive displacement dispenser. The positive displacement dispensers in each integrated cartridge 209, enable the production of a repeatable volume of fluid per actuation. The displaced volume of fluid from the cartridge enters the manifold 206 and is mixed with and combined with other biocompatible fluids, if any, from other integrated cartridges 209. The pressure in the manifold 206 is determined by the resistance to flow of the bulk fluid, which is affected by the characteristics of the downstream conduit, catheter, and patient's venous pressure. This embodiment enables the dispensing of multiple fluids to the patient without the need for the use of a system level pump 223 as illustrated in FIGS. 3 and 4. It should be appreciated by those skilled in the art that the positive displacement dispenser may be used with features of other embodiments, as for example those described in FIGS. 3 and 4.

It should be understood by those skilled in the art that devices embodying features of the present invention may include just bioactive fluids and/or infusion fluids and that the presence of both is not necessary to the practice of the invention.

Figure 6:
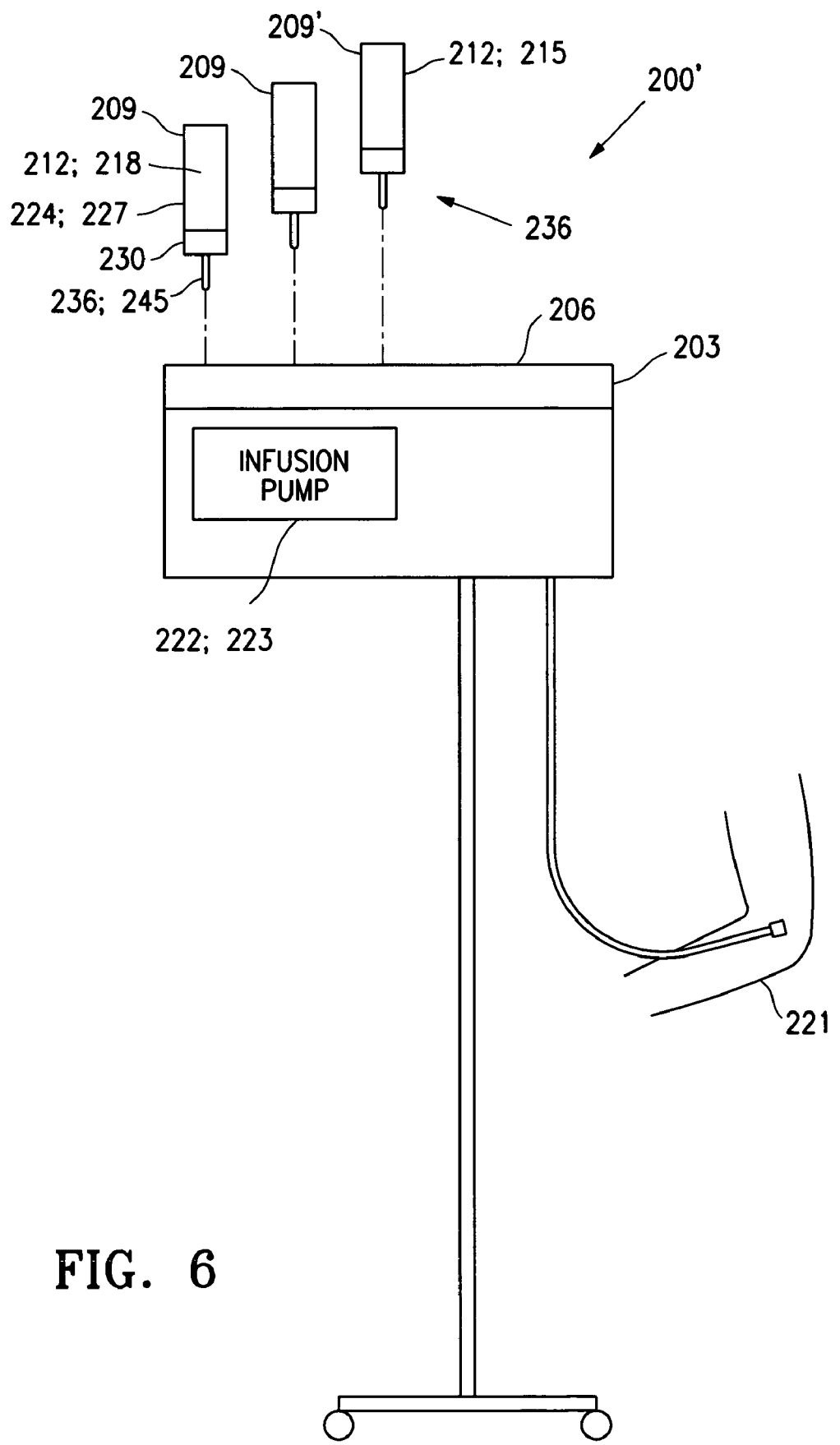
FIG. 6 is a schematic illustration of an alternative IV infusion system embodying features of the present invention.

FIG. 6 generally illustrates an infusion system 200' embodying features of the invention, and including the main system controller box 203, the manifold 206, and at least one integrated cartridges 209. In the embodiment shown, the infusion system 200', includes a plurality of integrated cartridges 209, one of which 209' is a source biocompatible fluid 212 such as infusion fluid 215 (e.g. saline solution), and one of which 209 is a source of biocompatible fluid 212 such as bioactive fluid 218. The infusion system as shown in FIG. 6 may incorporate a positive displacement pump configuration, such as that described in relation to FIG. 5.

Figure 7:
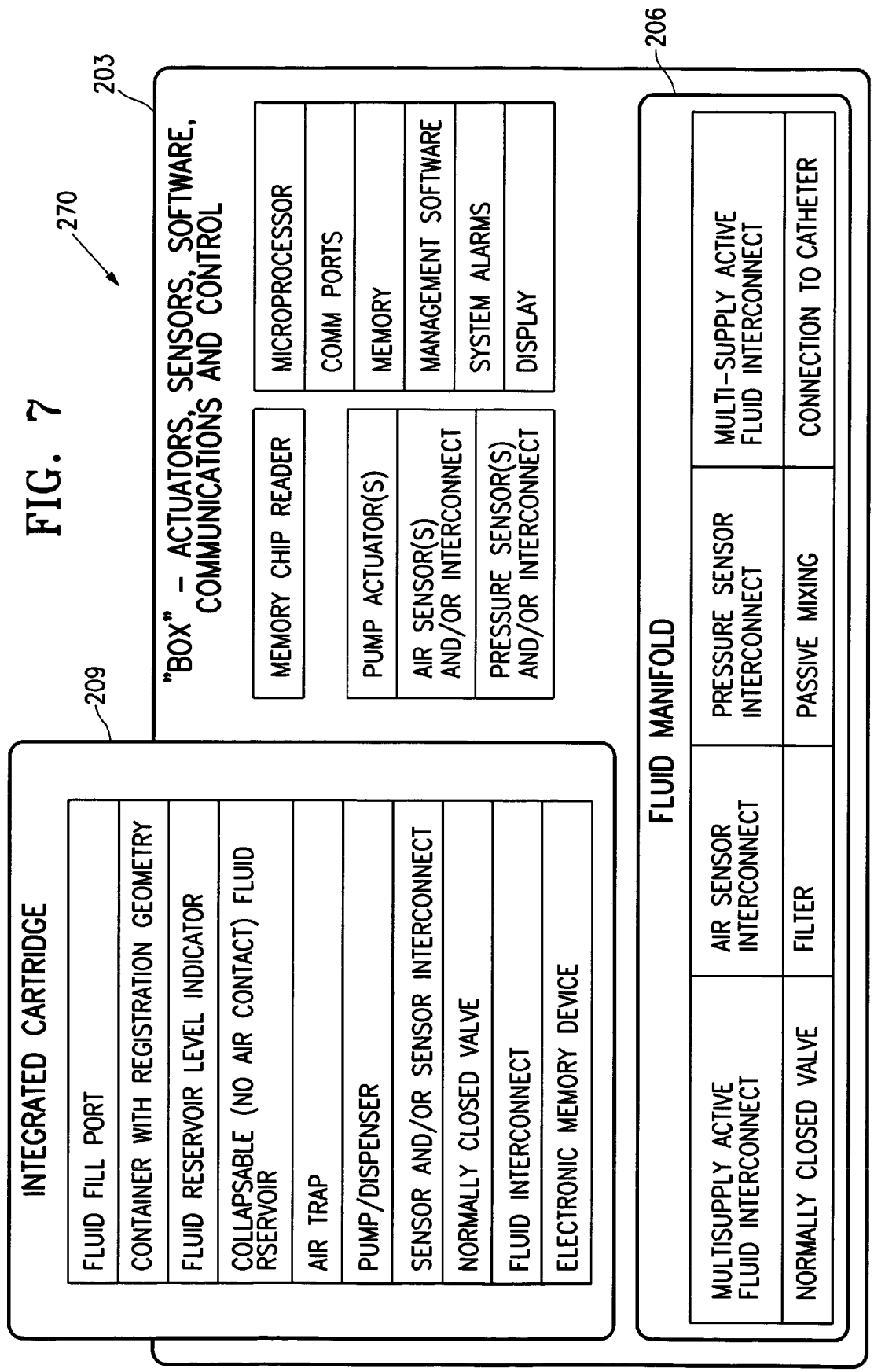
FIG. 7 is an exemplary block diagram of an IV infusion system embodying features of the present invention.

FIG. 7, represents an exemplary block diagram 270, illustrating features that may be present in one or more of the embodiments of an infusion system 200 or 200' according to the present invention. Although in the description following below, many components are provided and described, it should be appreciated by those skilled in the art, that neither all of the various components provided in the block diagram may necessarily be present in an apparatus according to the present invention nor that the list is an exhaustive list of all components that may be present.

In an embodiment, the integrated cartridge 209 is configured to perform at least one or more of the following functions: contain and dispense the biocompatible fluid, fluidically, preferably, removably, connect to the manifold; measure fluid pressure, prevent free flow of the biocompatible fluid through the assembly, separate and trap any air that may be present in the assembly, prevent contamination, display drug information, indicate fluid level, store prescription data, and fixture to the main system controller box for automatic and/or user interaction.

To perform the one or more of the above functions, the integrated cartridge 209, generally may include at least one or more of the following components (as for example shown in FIGS. 8 and 9): a fluid fill port, fluid reservoir level indicator, collapsible fluid reservoir, air trap, pump or dispenser, either or both and sensor interconnect, fluid interconnect, electronic memory device such as EEPROM, flash memory device, or other identifying means such as a barcode label or mechanical identification system, and a configuration having a registration geometry for connection with the main system controller box 203. In an embodiment, the integrated cartridge 209 may be configured to enable sterilization and/or is disposable or refillable, as for example, capable of undergoing cleaning and sterilization procedures sufficient to allow the integrated cartridge to be filled with same or different biocompatible fluids (e.g., bioactive fluids).

Figure 8:
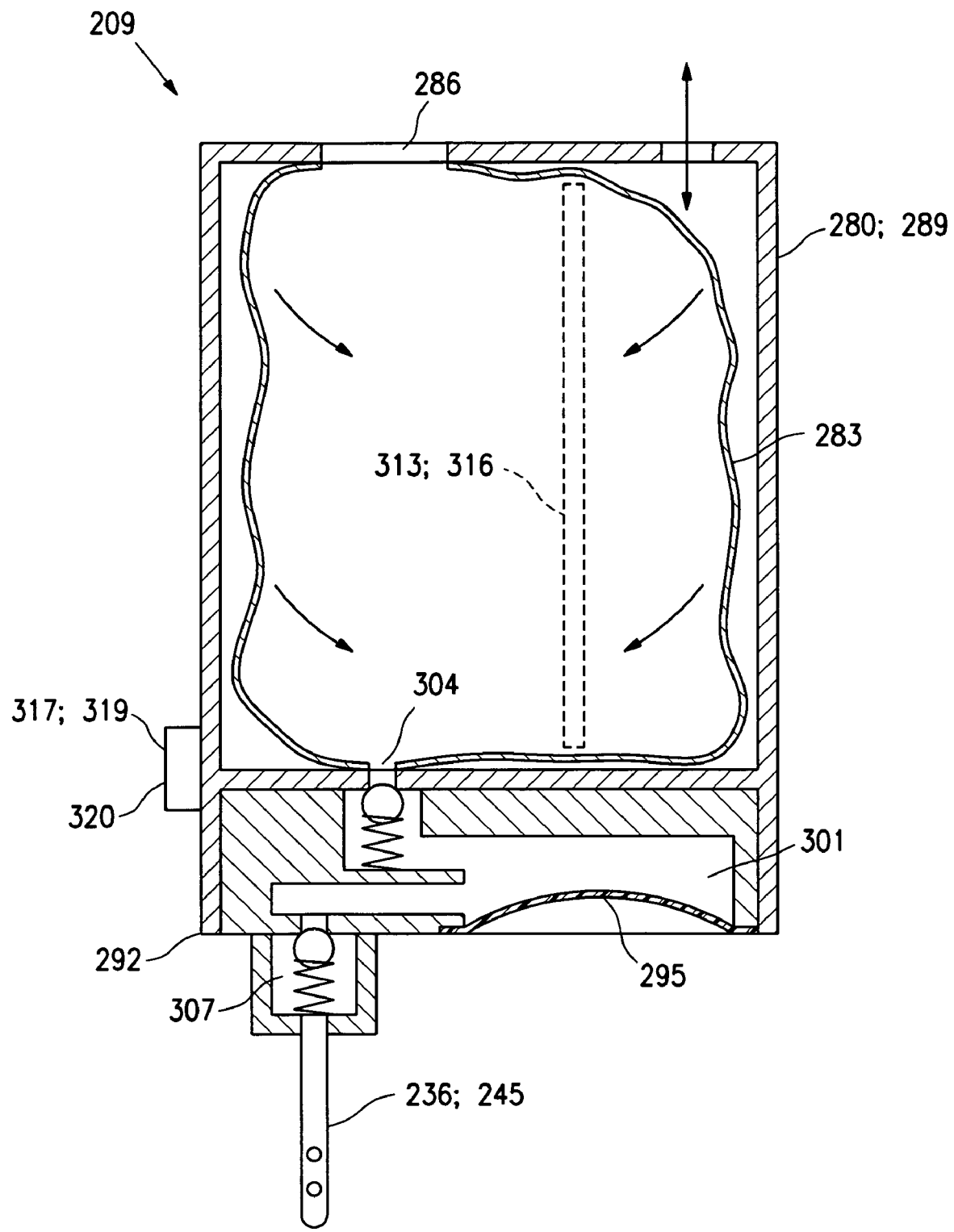
FIG. 8 is a schematic illustration of an integrated cartridge embodying features of the present invention.

The individual components in the integrated cartridge may be off the shelf or novel components. Various options exist for each of the components. By way of example, the reservoir indicator may be a translucent strip of plastic in the fluid reservoir 283 (e.g., as shown in FIG. 8) or additionally or alternatively a level sensor that displays the fluid level electronically. Suitable dispensers include diaphragm pumps, inkjet devices, and pressured air bladders providing motive force to the fluid.

In an embodiment, the manifold 206 is configured to perform at least one or more of the following functions: passive or active mixing of the fluids, connect to one or more biocompatible fluid supplies, manage air, measure fluid pressure, connect to the subject, prevent free flow of fluid to the subject, and prevent contamination.

To perform the one or more of the above functions, the manifold 206, generally may include at least one or more of the following components: multi-supply active fluid interconnect, a mechanical geometry to promote passive mixing, an active mixing element, air sensor interconnect, pressure sensor, filter, and a valve which is normally in closed configuration.

Figure 10:
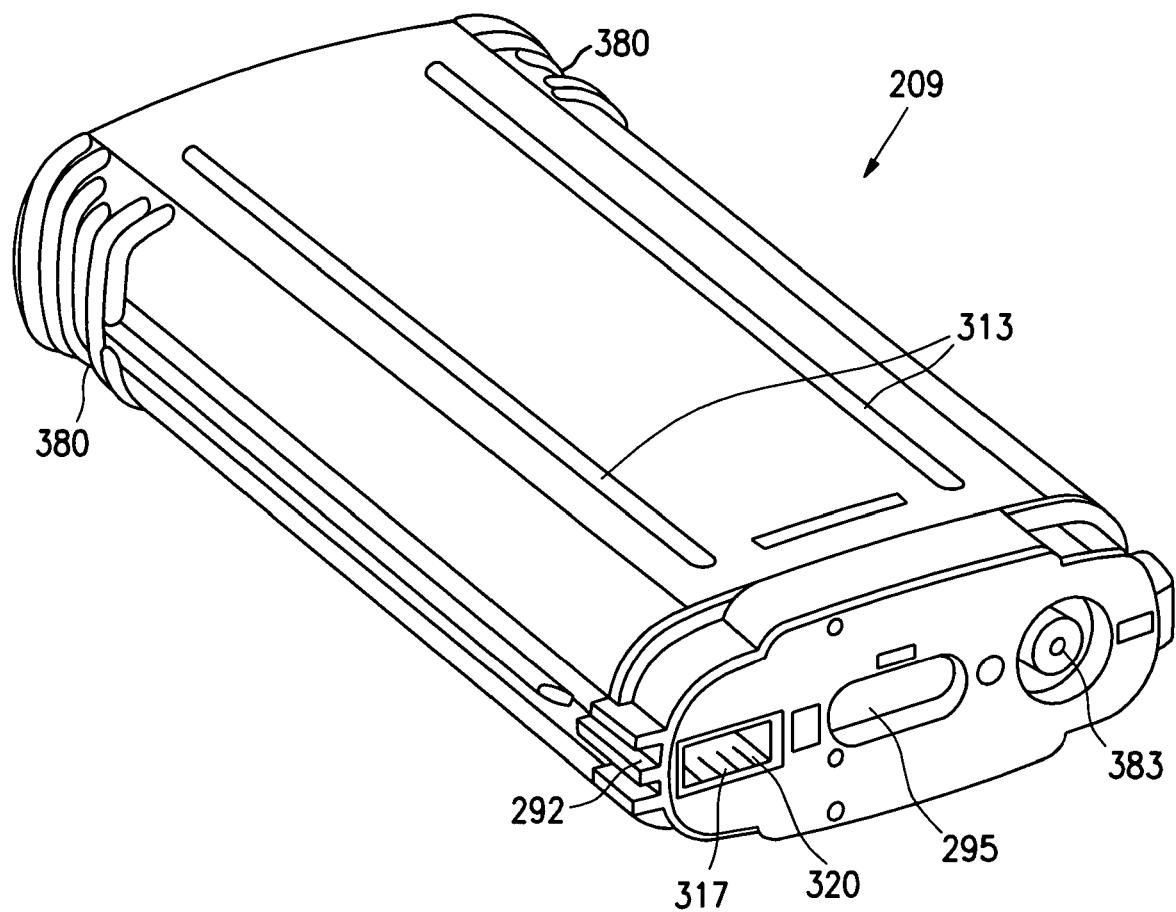
FIG. 10 is an illustration of an alternate integrated cartridge embodying features of the present invention.

In an embodiment, the main system controller box 203 is configured to include at least one or more of the following components: memory device reader, barcode reader, one or more dispenser actuators, one or more of either or both air sensor and sensor interconnects such as air and/or pressure sensors, microprocessor, communication ports, memory, management software, system alarms, and display. The system controller may serve as the main interface with the attendant for manual programming, if needed, stop and run operations, display information and other controls as may be necessary to properly operate the system. In an embodiment, the system controller 203 is configured to allow re-writing to the memory device (e.g., EEPROM, as shown in FIG. 10).

Now referring to FIG. 8, an integrated cartridge 209, embodying features of the invention is shown, including a fluid container 280 with an internal collapsible fluid reservoir 283 and a fluid fill septum 286 for receiving the fluid 212. In the embodiment shown, the container 280 is a hard shell container 289 with registerable datums, such as square datums 292, for registration in the main system controller box 203. The collapsible fluid reservoir 283 collapses within the fluid container 280 as fluid is dispensed from the cartridge 209. By way of example, the reservoir material may be a Class VI PVC material, which is sterilized during manufacturing to provide sterile containment of the fluid and reduce and/or eliminate the diffusion of air into the fluid. Volume replacement of the pumped fluid is provided by the collapsible bag reservoir 283. A diaphragm style pump membrane 295 and pumping chamber 301 with inlet 304 and outlet check valve 307 (normally in closed position as shown) are also shown. The diaphragm 295 is actuated by a plunger 310 (not shown), compressing the fluid in the chamber, forcing the fluid to be positively displaced at the outlet. In the embodiment described, the plunger 310 resides in the main system controller box 203. The plunger may be driven by a number of driving mechanisms such as a solenoid valve, a linear stepper or DC motor, or a cam. The plunger and the motor may receive an electrical signal from the main system controller box 203 to actuate the diaphragm pump (e.g., dispenser), causing a unit volume to be dispensed from the integrated cartridge into the manifold 206. In the embodiment shown, the interface between the main system controller box 203 and the integrated cartridge may be a mechanical one by way of the plunger and the flexible diaphragm. In the embodiment shown, the integrated cartridge further includes a fluid indicator 313 such as a visual fluid level indicator 316, and a memory device 317 such as EEPROM memory chip 319 and electrical contacts 320. Cartridge fluid interconnects 236, as for example needle 245, is configured for mating with the septum 248 in the manifold (such as that shown in FIGS. 5B and 9).

Now referring to FIG. 9, features of an alternate integrated cartridge 209 are shown, generally including a fluid container housing a quantity of biocompatible fluid 212, in a fluid reservoir 283. The reservoir may have any suitable size, generally ranging from 10 to 1000 milliliters (ml) in fluid volume. The container 280 has a dispenser 230, by way of example a dynamic dispenser such as a jet dispenser (e.g., thermal or piezo based, acoustic jet), elastomeric, peristaltic, or volumetric pump. The dispenser 230 is integral to the assembly, affixed thereto, and is fluidically connected to the fluid reservoir 283, forming together, an integrated fluid dispensing system 233. The fluid is dispensed into a sloped chamber 335 that is connected to the manifold 206 (the drip chamber) via needle 245 mating with septum 248. It is appreciated by those skilled in the art that although the manifold 206 is shown to be connectable to one integrated cartridge 209, it may be connectable to a plurality of integrated cartridges 209, such as integrated cartridge assembly 254, as described earlier above (e.g., FIG. 3). A regulator assembly 336 controls the backpressure in the integrated assembly. Several options exist for regulating the pressure. In the embodiment shown, a volume based regulator; such as that described in U.S. Pat. No. 5,852,459 including a flexible air bladder 338, one or more hinged plates 341 acting against the bladder 338 via spring 344 (not visible), and a hinged plate that opens pressure balancing valve 347.

A pressure balancing system 349 comprising a second needle 350 connects the manifold 206 to the firing chamber (sloped chamber) 335, the flexible air bladder 338, and the pressure balancing valve 347. This pressure balancing system enables the manifold and the firing chamber pressure to serve as a reference for the system and allows the spring, lever, bladder mechanism to maintain a negative backpressure in the supply. This pressure balancing system enables the use of dynamic dispensers such as TIJ, Piezo or other jet dispensing techniques. The integrated cartridge, as shown, includes a fluid fill port 356 that directly connects to reservoir 283. The fill port 356, as shown, comprises a plastic screw fitting with a large head for hand removal/install, a ball cork, or other such similar mechanisms.

The integrated cartridges, features of which are shown in FIGS. 8 and 9, include the electronic memory device 317, such as EEPROM 319, which may be programmed with patient, drug, and dosing information such as that disclosed in U.S. Patent Publication Number 20040254527A1, and assigned to the same assignee as that of the present invention. The integrated cartridge 209, as shown, has integral geometric features enabling alignment and engagement of the chip to the receiving contacts on the IV equipment set. Electrical connections to the IV equipment set are made to drive the dispenser via an interconnect circuit 359. In alternative embodiments, the electronic memory device may be RF (radio frequency) and/or IR (infrared) capable, such that no physical contacts are required. Alternatively or in addition, the integrated cartridge 209 may contain other unique identification mechanisms such as a barcode or mechanical key-lock identifier 361 (e.g., arrangement of tabs). By way of example, when inserted into the system controller 203, the controller 203, configured to scan and interpret the barcode information, reads the information on the barcode and sets or adjusts the fluid delivery parameters. As previously, discussed, the information may be encoded onto the memory device (e.g., EEPROM, flash memory, barcode, key-lock identifier) at any suitable location such as the factory, pharmacy, nursing station, or the patient's beside and thereafter travels with the integrated cartridge.

FIG. 9, as shown, further includes the fluid manifold 206 with the pressure tight receptacle 251 enabling fluidic coupling between the main IV solution and the system pump. It should be noted that the manifold as shown in this embodiment corresponds to an embodiment features of which are shown in FIG. 2, but that it is configurable for use with other embodiments. The receptacle 251, as shown, is formed of clear material to enable direct viewing of its contents, and shows a fluid line 362. The receptacle, as shown, can be manually or automatically (e.g., by way of optical detectors) verify the fluid level and dispensing. The manifold includes ports 248, elastomeric as shown, to accommodate the fluid receivable from the integrated cartridge 209. Other suitable means for actively sealing the ports, include, but are not limited to, spring loaded valves and the likes.

The manifold as shown, further includes an integrated outlet flexible conduit 365 such as tubing section to interface with the peristaltic or volumetric pump (shown in FIG. 2). The manifold further includes an integrated inlet IV bag spike 368 for connecting to the main IV fluid supply (shown in FIG. 2).

Now referring to FIG. 10, an integrated cartridge 209 embodying features of the present invention is illustrated, including finger grips 380, visual fluid level indicators 313, a memory device 317 such as EEPROM 319, registerable datum 292, and pump membrane 295. The integrated cartridge 209 further includes liquid outlet 383 for fluidic connection to the manifold.

By way of an exemplary operation, one or more integrated cartridges are inserted into the manifold and fluid connections are made via the needle/septum ports (or other alternative active sealing interconnects such as spring loaded). The memory device or other identification means is interpreted by the main system controller and the dispensing profile is automatically programmed, and at least any one or more of information regarding the drug, the patient, and other prescription specific data is verified and/or validated (such as day or time of use, route, precautions, etc.). This automatic programming and validation may be performed for each and/or all cartridges installed in the system. The administration program and information is displayed on the controller box for confirmation by the nurse or attendant. The administration may begin after priming the system and confirmation of the delivery program, as necessary.

Each cartridge, as appropriate, dispenses fluid into the manifold. For cartridges with positive displacement pumps, such as those illustrated in FIG. 5A, 5B, 8, or 10, a unit volume of fluid will be dispensed into the manifold during each actuation. The collective fluids dispensed by one or more cartridges will be combined in the manifold and delivered to the patient. The pressure in the manifold will be determined by the downstream flow resistance (patient venous pressure, length and size of catheter, etc.). If at any time the manifold pressure exceeds a pre-determined limit that could be the result of an unwanted event (e.g., occlusion), the system pressure sensor is read by the system controller and an alarm mechanism may be prompted, notifying the attendant of possible problems, allowing for investigation and resolution of the problem before additional delivery is made to the subject.

In the event of a low fluid level in a single cartridge, either by alarmed detection or visual indication, the attendant may activate a cartridge replacement routine via the interface and then physically remove the cartridge. In the embodiment utilizing fluid interconnects with an active surface (e.g., elastomeric septum), the interconnect reseals upon removal of the cartridge with little or no pressure loss in the manifold, while allowing the continuation of delivery of other fluids from other cartridges, as the case may be. Upon insertion of a new supply cartridge, the system controller again reads the cartridge memory device, prepares the program and prompts the attendant to validate the administration program. Upon verification, the newly replaced cartridge begins dispensing the fluid per the administration plan.

The system controller manages all fluids when multiple cartridges are installed. The controller may incorporate criteria such as minimum/maximum fluid volume delivery rate to patient, minimum/maximum single fluid bolus delivery, minimum/maximum manifold volume, minimum/maximum dose delay, and continuity requirements; into the planned program. This planned program and administration method is enabled by the use of integrated cartridges with a memory device, as the appropriate dose information is available from the cartridge. In an embodiment, the system controller may have an interface to allow for manual control of the dispensing profiles when desired by the attendant.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

Terms such a "element," "member," "component," "device," "section," "portion," "step," "means," and words of similar import, when used herein shall not be construed as invoking the provisions of 35 U.S.C. §112(6) unless the following claims expressly use the term "means" followed by a particular function without specific structure or the term "step" followed by a particular function without specific action. Accordingly, it is not intended that the invention be limited, except as by the appended claims.

What is claimed is:

1. An integrated cartridge assembly for delivery of biocompatible fluids to a subject, comprising:
   at least two replaceable integrated cartridges;
   a single manifold fluidically, removably and simultaneously connectable to the at least two integrated cartridges; and
   a system controller for setting, adjusting and actuating delivery of the biocompatible fluids to the subject by the integrated cartridge assembly, the system controller being structurally associated with the single manifold and configured to scan and interpret information encoded on the at least two integrated cartridges when the at least two integrated cartridges are connected to the single manifold, the system controller's setting and adjusting delivery of the biocompatible fluids to the subject by the integrated cartridge assembly being enabled by the information encoded on the at least two integrated cartridges;
   wherein each cartridge includes:
   a. a fluid reservoir for housing an individual biocompatible fluid;
   b. a dispenser substantially permanently and fluidically connected to the fluid reservoir and including a positive displacement pump configuration for dispensing the individual biocompatible fluid to the manifold by receiving a pumping force on the individual biocompatible fluid from an actuator of the system controller via a mechanical interface between the actuator and the cartridge, the pumping force controlling flow and pressure of the individual biocompatible fluid and producing a controllable and repeatable fluid volume from the dispenser; and c. a memory device for encoding information read by the system controller about the individual biocompatible fluid in the cartridge.

2. An assembly according to claim 1, wherein the memory device is an electronic memory device.

3. An assembly according to claim 2, wherein the electronic memory device is an electronically erasable programmable read-only memory device.

4. An assembly according to claim 2, wherein the electronic memory device is re-writable.

5. An assembly according to claim 1, wherein the memory device comprises a bar code.

6. An assembly according to claim 1, wherein the memory device comprises a mechanical means for storing information.

7. An assembly according to claim 1, wherein the individual biocompatible fluid in at least one of the fluid reservoirs includes a bioactive fluid including a drug.

8. An assembly according to claim 1, wherein the individual biocompatible fluid in at least one of the fluid reservoirs consists essentially of an infusion fluid.

9. An assembly according to claim 1, wherein the manifold is configured for fluidic connection to a main supply of biocompatible fluid.

10. An assembly according to claim 1, wherein the manifold is configured for fluidic connection to a system pump for controlling flow and pressure of at least one of the biocompatible fluids to the subject.

11. An assembly according to claim 1, wherein each integrated cartridge is configured to positively displace fluid and control flow of the individual biocompatible fluid to the subject through the manifold without requiring the need of a separate main pump generally locatable between the manifold and the subject.

12. An assembly according to claim 1, wherein each integrated cartridge has a registerable geometry.

13. An assembly according to claim 1, wherein the fluid reservoir has a level indicator or sensor.

14. An assembly according to claim 1, wherein the fluid reservoir is collapsible and provides an air barrier.

15. An assembly according to claim 1, wherein each integrated cartridge includes a sensor interconnect or sensor.

16. An assembly according to claim 1, wherein the connection between the fluid reservoir and the dispenser is made by way of a matched pair of fluid interconnects.

17. A manifold for delivery of at least one biocompatible fluid to a subject, comprising:

a. a receptacle for receiving and dispatching one or more biocompatible fluids;

b. at least two manifold fluid interconnects configured to fluidically, removably and simultaneously connect the receptacle to at least two integrated cartridges, each interconnect connecting to one replaceable integrated cartridge, each integrated cartridge comprising a fluid reservoir for housing an individual biocompatible fluid and a dispenser substantially permanently and fluidically connected to the fluid reservoir;

wherein the manifold interconnect is connected to the dispenser which dispenses the individual biocompatible fluid to the manifold by receiving a pumping force on the individual biocompatible fluid in the fluid reservoir from an actuator of a system controller via a mechanical interface between the actuator and the cartridge, the pumping force controlling flow and pressure of the individual biocompatible fluid and producing a controllable and repeatable fluid volume from the dispenser to the manifold; and wherein the manifold is structurally associated with the system controller, the system controller setting, adjusting and actuating delivery of the biocompatible fluids to the subject by being configured to scan and interpret information encoded on the at least two integrated cartridges when the at least two integrated cartridges are connected to the manifold, the system controller's setting and adjusting delivery of the biocompatible fluids to the subject being enabled by the information encoded on the at least two integrated cartridges.

18. The assembly of claim 1 wherein each of the at least two replaceable integrated cartridges is independently removable from the single manifold during use of the assembly.

* * * * *